United States Patent [19]

Levius

[11] Patent Number: 4,875,472
[45] Date of Patent: Oct. 24, 1989

[54] FLAT COIL SPRING PENILE PROSTHESIS

[75] Inventor: Dezso K. Levius, Bloomington, Minn.

[73] Assignee: American Medical Systems, Inc., Minnetonka, Minn.

[21] Appl. No.: 131,364

[22] Filed: Dec. 10, 1987

[51] Int. Cl.⁴ .............................................. A61F 2/26
[52] U.S. Cl. ..................................................... 128/79
[58] Field of Search .................... 128/79; 604/281, 282

[56] References Cited

U.S. PATENT DOCUMENTS

| | | | |
|---|---|---|---|
| 4,267,829 | 5/1981 | Burton et al. | 128/79 |
| 4,545,081 | 10/1985 | Nestor et al. | 128/79 |
| 4,590,927 | 5/1986 | Porter et al. | 128/79 |
| 4,693,719 | 9/1987 | Franko | 128/79 |

Primary Examiner—John J. Wilson
Assistant Examiner—Cary E. Stone
Attorney, Agent, or Firm—Peter C. Richardson; Lawrence C. Akers; Gezina Holtrust

[57] ABSTRACT

A prosthesis to be implanted in the penis for simulating an erection is disclosed. The prosthesis has at least one cylinder to be implanted in the corpora cavernosa. A flat coil spring is contained within the cylinder. When uncompressed, the spring allows the cylinder and the penis to remain flaccid. When compressed, the spring forms a rigid column that erects the cylinder and the penis and resists bending under pressure. The spring is preferably compressed by inflating an expandable chamber adjacent to the spring within the cylinder.

9 Claims, 3 Drawing Sheets

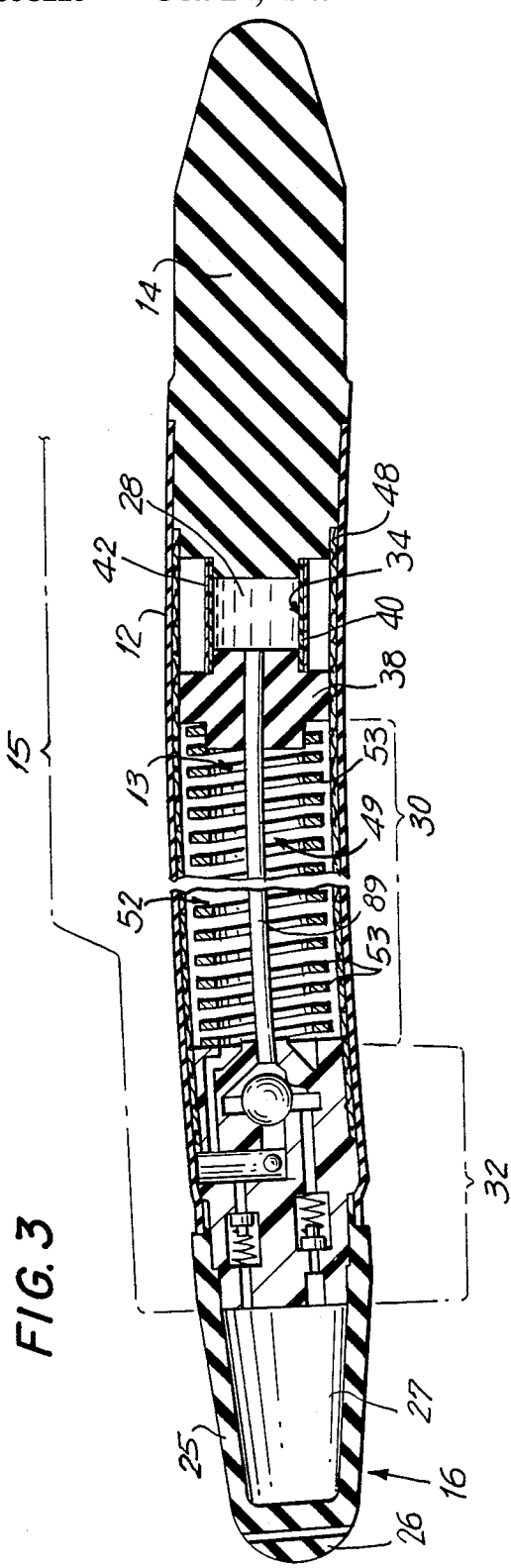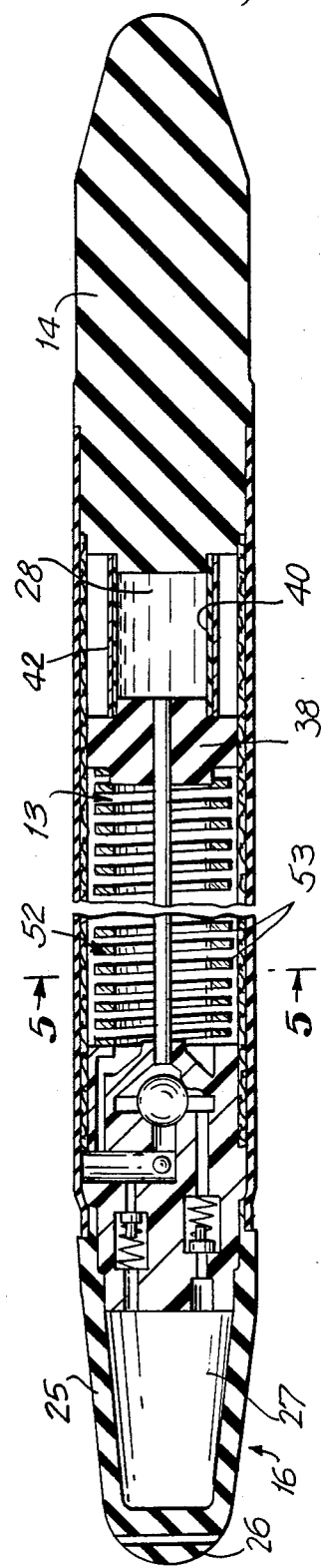
FIG. 3
FIG. 4

FLAT COIL SPRING PENILE PROSTHESIS

BACKGROUND OF THE INVENTION

The present invention relates generally to methods and devices for alleviating erectile impotence. More particularly, the present invention relates to a novel implantable penile erectile system.

A number of devices are available to enable those with erectile impotence to achieve an erection. The devices are generally implanted within the corpus cavernosum of the penis. Normally two such devices are used, one implanted into each corpus cavernosum.

Modern day devices evolved from early rigid rod devices. Rigid rod devices alleviated erectile impotence; however, the rigid rod produced a permanent erection that often embarrassed the user. Malleable or bendable rods at least partially alleviated the problem. The user of a malleable prosthesis can bend the penis down; however, the user still has a hard penis.

Inflatable penile prostheses were developed to avoid the user having a constantly hard penis. Inflatable penile prostheses generally include a cylinder within the corpus cavernosum that is substantially deflated in the flaccid state. The user produces an erection by manually pumping fluid into the cylinder to inflate the cylinder.

SUMMARY OF THE INVENTION

The prosthesis of the present invention also has a flaccid and an erect state. The penile cylinders of a preferred embodiment of the present invention have a substantially solid proximal portion and a pump at the distal end. Between the proximal portion and the pump are an axially expandable chamber and an adjacent flat coil spring. The spring lies substantially along the body plane when the prosthesis is implanted.

When the axially expandable chamber is compressed, or not expanded, the adjacent spring has spaces between the coils and the device assumes a relaxed, limp condition. When implanted in the penis, the penis is substantially limp at and distal to the body plane and bends in an arc to a flaccid position depending on the spaces between the coils. When fluid is pumped into the chamber, the chamber becomes pressurized and expands axially to compress the coils of the spring. Because the axial expansion required to compress the spring is minimal, the chamber is relatively small. When compressed, the coils of the spring align to form a rigid column adjacent to the pressurized chamber. The compressed coils of the spring form a column that is very stiff and resists bending.

The prosthesis of the present invention can be unitary, with no separate pump, or adapted to attach to a separate pump. A number of means, such as mechanical means, may be used to compress the spring.

BRIEF DESCRIPTION OF THE DRAWINGS

FIG. 3 is an enlarged vertical cross-sectional view taken generally along curve 3—3 in FIG. 1.

FIG. 4 is an enlarged vertical cross-sectional view taken generally along line 4—4 of FIG. 2.

DESCRIPTION OF A PREFERRED EMBODIMENT

Figure 2:
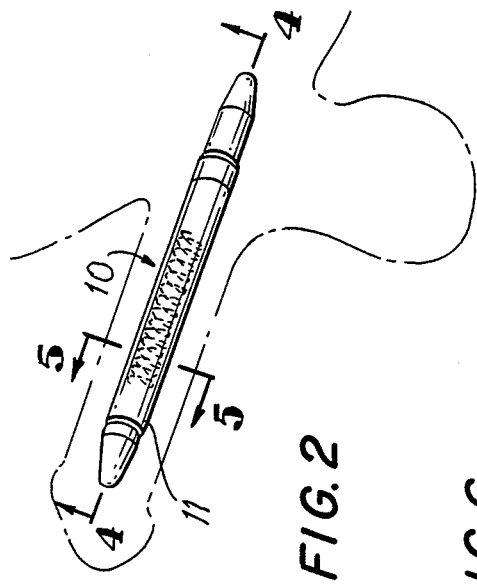
FIG. 2 is a partially cut-away side elevational view of the embodiment of FIG. 1 in an erect state.
Figure 6:
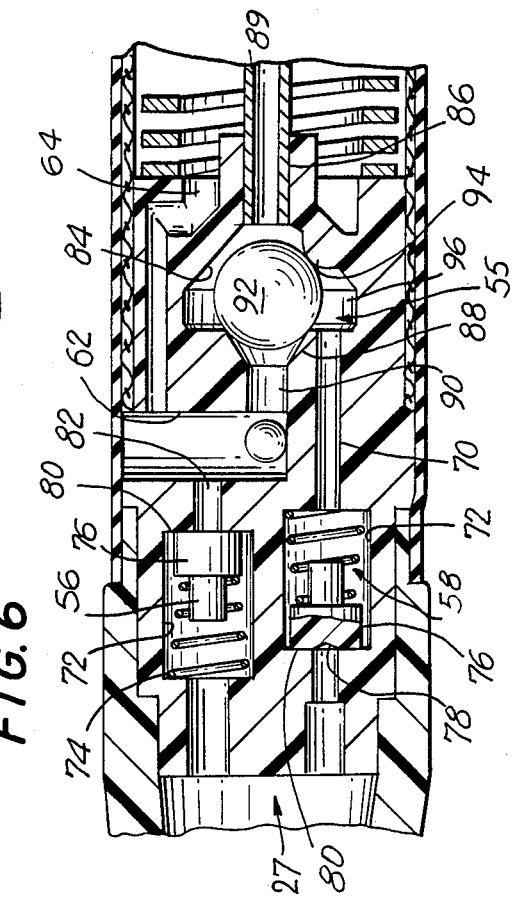
FIG. 6 is an enlarged cross-sectional view of the valve plug of the prosthesis shown in FIG. 3.

Referring to the drawings, like reference characters are used for like parts throughout the several views.

Figure 1:
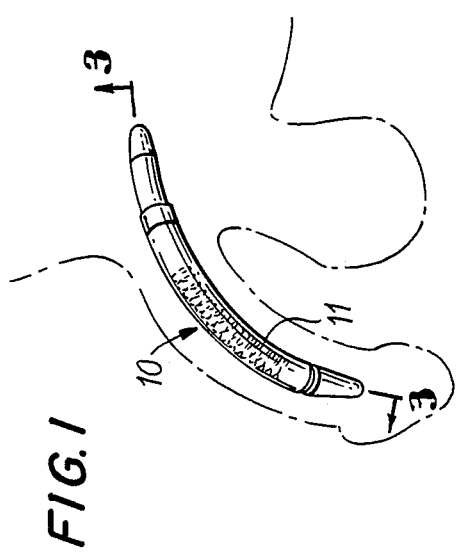
FIG. 1 is a partially cut-away side elevational view of a preferred embodiment of the present invention, in use, in its flaccid state.
Figure 5:
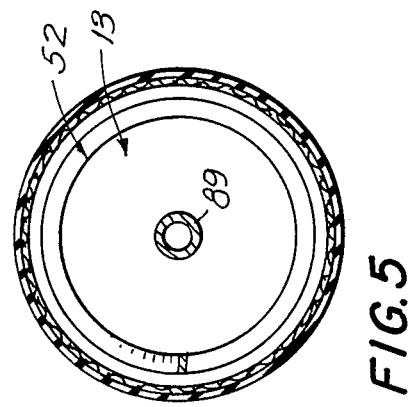
FIG. 5 is a cross-sectional view along line 5—5 of FIG. 4.
Figure 7:
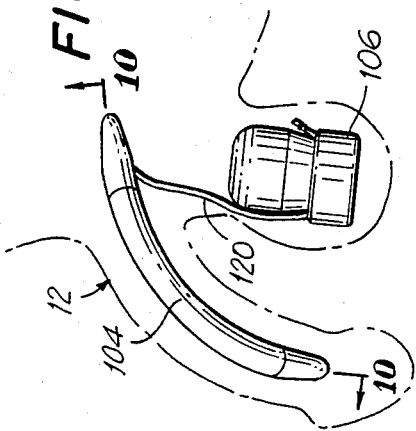
FIG. 7 is a side elevational view of an alternate embodiment of the present invention in its flaccid state.
Figure 8:
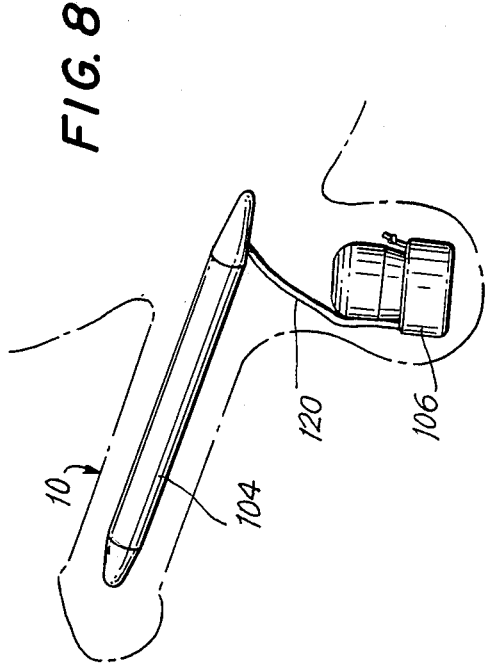
FIG. 8 is a side elevational view of the embodiment of FIG. 7 in its erect state.

The slinky penile prosthesis 10 shown in FIGS. 1–6 is a self-contained cylinder 11 designed to be implanted in the corpus cavernosum of the penis. Normally, two cylinders will be implanted, one in each corpus cavernosum; however, the present invention is adaptable for use with double cylinder designs in which one prosthesis is used to fill both corpus cavernosa. FIG. 1 depicts cylinder 11 inside of the penis in a flaccid state. FIG. 2 depicts cylinder 11 and the penis in a rigid, erect state.

As seen in FIG. 3, a cylinder 11 comprises a proximal section 14, a medial section 15 and a distal section 16. An outer layer 12 composed of a biocompatible material, such as medical grade silicone elastomer, extends between proximal section 14 and distal section 16 to form an enclosure 13. Proximal section 14 is substantially solid, preferably made of silicone, and normally is positioned in the rear of the corpus cavernosum under the puboischiatic rami.

Distal section 16 ha a substantially rigid casing 25 and a front tip 26 that is substantially rigid, to resist buckling during intercourse. Casing 25 may be made of a number of materials, preferably silicone. Front tip 26 may be made substantially solid, if desired. Casing 25 defines a pump 27.

Medial section 15 has three components: an axially expandable chamber 28; a spring section 30; and a valve plug 32. Chamber 28 is defined by a tubular portion 34 abutted at the proximal end by proximal section 14 and at the distal end by a distal plug 38. Distal plug 38 is substantially rigid and may be made of any suitable material, preferably silicone. Tubular portion 34 may be formed of two layers including an inner layer 40 and an outer sheath 42. Inner layer 40 may be formed of a substantially fluid impervious material, preferably silicone. Outer sheath 42 should expand longitudinally, but is preferably substantially radially non-distensible to minimize the volume of fluid necessary to expand chamber 28. Outer sheath 42 should preferably not crimp or wrinkle when compressed. A preferable material for outer sheath 42 is polytetrafluoroethylene ("PTFE") although other suitable materials may be used. For example, outer sheath 42 may be composed of vascular graft from Impra, Inc., Tempe, Ariz. or vascular graft from W. L. Gore & Associates, Inc., Newark, Del.

Adjacent distal ends of inner layer 40 and outer sheath 42 are sealingly engaged with distal plug 38. Adjacent proximal ends of inner layer 40 and outer sheath 42 are sealingly engaged with proximal section 14.

A nondistensible sheath 48 surrounds medial section 15 to define a medial tube 49. Nondistensible sheath 48 may be made of a variety of materials, but advantageously may be made of woven dacron material, such as prosthetic vascular graft. Distal plug 38 substantially fills but has freedom of axial movement within medial tube 49.

Anchored to and extending between distal plug 38 and valve plug 32 is a flat coil spring 52. Spring 52 preferably has an outer diameter ranging between 0.2–0.4 inches and a coil width ranging between 0.05–0.15 inches. Spring 52 may be obtained from any standard source, such as Smalley Steel Ring Co., Wheely, Ill. Spring 52, like distal plug 38, has freedom of axial movement within medial tube 49.

Spring 52 is positioned along the length of cylinder 11 so that it tends to lie substantially along the body plane when implanted. Tubular portion 34, distal plug 38, and spring 52 extend within medial tube 49 and between proximal section 14 and valve plug 32 in an unsupported fashion. When chamber 28 is compressed, or not expanded, the coils 53 of spring 52 are spaced apart as shown in FIGS. 1 and 3. Chamber 28 and spring 52 remain substantially limp, allowing cylinder 11 and the penis to achieve a flaccid state as shown in FIG. 1.

Valve plug 32 may take a number of forms. A preferred embodiment of valve plug 32 is shown in FIG. 3, and is an adaptation of the valve plug described in U.S. Pat. No. 4,590,927 incorporated herein by reference. Valve plug 32 of FIG. 3 is enlarged and shown in FIG. 6. Valve plug 32 includes a bypass valve 55, an inlet valve 56, and an outlet valve 58. Inlet valve 56 communicates at its distal end with pump 27 of distal section 16. Inlet valve 56 communicates at its proximal end with a radially oriented passageway 62. Passageway 62 communicates with an axial, lengthwise passageway 64. Axial passageway 64 also communicates with spring section 30. Regardless of the state of axially expandable chamber 28, communication through axial passageway 64 is always possible.

Outlet valve 58 communicates with distal section 16 on the distal end and communicates on the proximal end with bypass valve 55. A continuously open passageway 70 extends through bypass valve 55.

Inlet and outlet valves 56, 58 include an enlarged housing 72, a coiled spring 74, and a valve member 76. Coiled spring 74 biases valve member 76 of outlet valve 58 distally and coiled spring 74 of inlet valve 56 biases valve member 76 proximally. Sealing faces 78 of valves 56, 58 seal on an adjacent transversely oriented ledge 80. Sealing faces 78 of valves 56, 58 are concave to encourage a good seal. Valves 56, 58 each include a necked down region 82 in housing 72 proximate ledge 80.

Bypass valve 55 includes a generally conical housing 84 with a proximally extending port 86 and a distally extending seat 88. Port 86 is sealingly engaged to an inner axial passageway 89 that extends through spring section 30, distal plug 38, and into chamber 28. Passageway 89 is composed of a flexible, substantially fluid impervious material such as silicone. Seat 88 is generally conical and communicates with passageway 90 which in turn communicates with passageway 62. A ball 92 is normally seated on seat 88 closing passageway 90. One or more extensions 94 defined on conical housing 84 aligned with passageway 96 permit generally continuous fluid communication between passageway 96 and chamber 28 via port 86 and inner axial passageway 89. Reverse flow into passageway 90 is normally prevented by ball 92.

The prosthesis is operated as follows: A sufficient amount of fluid, such as physiological saline, is loaded into distal section 16, spring section 30, and chamber 28. Fluid may be loaded into distal section 16 and then pumped to spring section 30 and chamber 28. In any case, chamber 28 preferably should contain approximately 40–60% of its capacity in the flaccid state.

Distal section 16 and spring section 30 are filled with enough fluid so that, when fluid is pumped from distal section 16 and spring section 30 into chamber 28, chamber 28 longitudinally expands between 1–2.5 cm, preferably 1 cm. The longitudinal expansion should compress spring 52 and rigidize cylinder 11. The fluid volume needed for a particular device will be easily determined in practice by one of skill in the art.

Prosthesis 10 is then implanted within the corpus cavernosum of the patient. This may be done using conventional surgical techniques well known in the implantation of inflatable penile prostheses. Proximal section 14 is positioned in the rear region of the corpus cavernosum and distal section 16 in the distal region of the corpus cavernosum. It may be necessary to attach rear tip extenders to proximal section 14 in a fashion well known in the art in order to achieve a correct fit.

In order to operate the implanted prosthesis 10, the user squeezes distal section 16 by squeezing the distal end of the penis. The compression of distal section 16 forces fluid into chamber 28. The pressure increase within distal section 16 forces outlet valve 58 open allowing fluid to flow around valve member 76 through passageway 70 past ball 92, around extension 94 and through passageway 89 into chamber 28. The user may continue to successively squeeze distal section 16 until the pressure within chamber 28 becomes sufficiently great that valve member 76 no longer unseats from the sealing surface 78. At the same time, the compression of distal section 16 seals inlet valve 56 closed.

Casing 25 springs back to its original position after each squeeze of distal section 16, creating suction within pump 27. The suction opens inlet valve 56 and draws fluid from spring section 30 through passageway 64 and into pump 27. When the suction subsides, valve 56 springs closed.

When distal section 16 is successively squeezed, fluid is pumped into chamber 28. Tubular portion 34 expands longitudinally, increasing its length by between 1–2.5 centimeters, preferably 1 centimeter. In any event, tubular portion 34 expands enough to compress spring 52 to form a substantially rigid column. Because outer sheath 42 is substantially radially nondistensible, only a small volume of fluid is required to expand and rigidize chamber 28. Flat sided coils 53 compress to form a rigid column as shown in FIG. 4. The rigidity of expanded chamber 28 and compressed spring 52 causes prosthesis 10 and the penis to become erect, as shown in FIG. 2.

To resume the flaccid state after erection, valve plug 32 is squeezed externally. As a result of the deformation of conical housing 84 and seat 88, fluid flows from chamber 28 through passageway 89 past ball 92 and into passageway 90. From there the fluid may flow through passageway 62 to passageway 64. Because of the pent up pressure within chamber 28, the fluid is forced rearwardly through passageway 64 into spring section 30 where it is stored for use in the next erection. When the pressure within chamber 28 has subsided sufficiently, manual actuation of bypass valve 55 no longer has any effect on fluid outflow from chamber 28. Prosthesis 10 has reached equilibrium. Relaxed spring 52 acts essentially as a hinge, allowing prosthesis 10 and the penis to become flaccid and to bend along spring section 30, as shown in FIG. 2.

Figure 9:
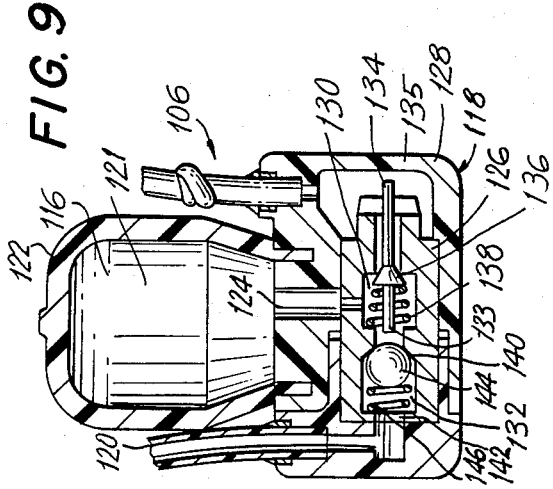
FIG. 9 is an enlarged vertical cross-sectional view of a preferred embodiment of the pump of FIGS. 7–8.
Figure 10:
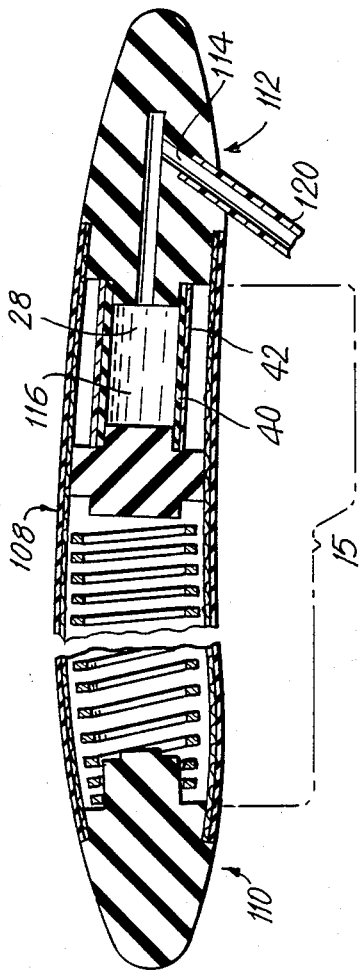
FIG. 10 is an enlarged vertical cross-sectional view taken along curve 10—10 of FIG. 7.

Referring now to FIGS. 7-10, an alternate embodiment of the present invention is depicted. The prosthesis 104 of this embodiment has a separate fluid supply means 106. Referring to FIG. 10, the cylinder 108 of this embodiment includes a distal section 110, a proximal section 112, and a medial section 15. Distal and proximal sections 110, 112 are preferably solid and may be composed of any suitable material such as silicone. Proximal section 112 has a passageway 114 through which fluid is allowed to flow from fluid supply means 106 through proximal section 112 and into chamber 28 of medial section 15.

Medial section 15 has the same construction and works in substantially the same manner as medial section 15 of FIGS. 1-5, with the exception that valve plug 32 and distal section 16 of FIGS. 1-5 are replaced with substantially solid distal section 110 and proximal section 14 is replaced by proximal section 112. No fluid is retained in spring section 30 of this embodiment.

Fluid supply means 106 may take a variety of forms that may be readily ascertained by one of skill in the art. A preferred embodiment is shown in FIG. 9. Another example is the pull valve and system described in U.S. Pat. No. 4,224,934 to Scott and Burton, incorporated herein by reference.

FIG. 9 depicts fluid supply means 106 as having a manually compressible pump means 116, a valve means 118 and demand tubing 120. Pump means 116 includes a reservoir 121 defined within a pump 122. Pump 122 communicates with valve means 118 through a port 124. Port 124 communicates with demand tubing 120 via valve 126 housed within a casing 128. Valve 126 defines two chambers 130, 132 connected by a port 133. Chamber 130 houses a rod 134 that extends laterally within chamber 130 between the wall 135 of casing 128 and into port 133. Rod 134 has an annular lip 136 biased away from chamber 132 in the resting state by a spring 138.

Chamber 132 has a seat 140 proximal to chamber 130 and communicates with a port 142 distal to chamber 130. Port 142 communicates with demand tubing 120 and thereby with chamber 28 in cylinder 108. A ball 144 is normally biased against seat 140 by a spring 146. In the resting state, fluid communication between demand tubing 120 and reservoir 121 is blocked by ball 144.

To operate prosthesis 104, pump 122 is squeezed and fluid flows through port 124 and chamber 130. The fluid pressure forces ball 144 away from seat 140, allowing fluid to flow through chamber 132, through port 142 into demand tubing 120, through passageway 114 in proximal section 112, and into chamber 28. Pump 122 is successively squeezed until chamber 28 expands to compress spring 52 and to erect the penis.

To end the erection, valve means 118 is squeezed laterally, as shown by the arrows in FIG. 9. Wall 135 forces annular lip 136 of rod 134 against spring 138. Rod 134 moves laterally against ball 144 to force ball 144 against spring 146 and away from seat 140. Fluid flows under pressure from chamber 28, through passageway 114, through demand tubing 120, port 142, chamber 132, port 133, chamber 130, port 124 and into reservoir 121. Once the pressure in chamber 28 is relieved, spring 52 and the penis become limp.

Spring 52 also can be mechanically compressed, for example, using an adaptation of the means depicted in copending application Ser. No. 076,354, filed on July 22, 1987, inventor Dezso K. Levius.

The foregoing description has been for purposes of illustration. Those skilled in the art will appreciate a number of variations and modifications therefrom. The following claims are intended to cover all modifications and variations within the true spirit and scope of the present invention.

What is claimed is:

1. A penile prosthesis comprising:
   at least one cylinder within at least one corpus cavernosum of the penis, said cylinder(s) having a distal portion for mounting in the distal portion of said penis and a proximal portion for mounting in the proximal portion of said penis;
   at least one flat coil spring contained in a spring section of said cylinder(s), said spring section lying substantially at or distal to the junction of said distal and said proximal portion of said cylinder(s); and
   means for reversibly compressing and relaxing said flat coil spring such that said cylinder(s) can be reversibly changed between a rigid and a flaccid state.

2. The prosthesis of claim 2 wherein said means for compressing and relaxing said flat coil spring comprises:
   an expandable chamber located adjacent to said flat coil spring within said cylinder(s); and
   means for expanding said chamber.

3. The prosthesis of claim 2 wherein said chamber comprises:
   a distal plug, axially movable within said cylinder(s); and
   a tubular portion anchored to and extending between a proximal section and said distal plug to define said chamber.

4. The prosthesis of claim 3 wherein said chamber is axially expandable but substantially radially nondistensible.

5. The prosthesis of claim 3 wherein said expanding means comprises means for reversibly pumping fluid into said chamber.

6. The prosthesis of claim 3 wherein said expanding means comprises:
   fluid contained within said spring section and said distal portion of said cylinder(s); and
   means for reversibly pumping said fluid into said chamber.

7. The prosthesis of claim 2 wherein said chamber is axially expandable but substantially radially nondistensible.

8. The prosthesis of claim 2 wherein said expanding means comprises means for reversibly pumping fluid into said chamber.

9. The prosthesis of claim 2 wherein said expanding means comprises:
   fluid contained within said spring section and said distal portion of said cylinder(s); and
   means for reversibly pumping said fluid into said chamber.

* * * * *